US007303909B2

(12) United States Patent
Heim et al.

(10) Patent No.: US 7,303,909 B2
(45) Date of Patent: Dec. 4, 2007

(54) BINARY VECTORS FOR THE IMPROVED TRANSFORMATION OF PLANTS SYSTEMS

(75) Inventors: Ute Heim, Gatersleben (DE); Karin Herbers, Quedlinburg (DE); Irene Kunze, Gatersleben (DE)

(73) Assignee: SunGene GmbH & Co. KGaA, Gatersleben (DE)

( * ) Notice: Subject to any disclaimer, the term of this patent is extended or adjusted under 35 U.S.C. 154(b) by 699 days.

(21) Appl. No.: 10/311,885

(22) PCT Filed: Jun. 28, 2001

(86) PCT No.: PCT/EP01/07359

§ 371 (c)(1),
(2), (4) Date: Jan. 14, 2003

(87) PCT Pub. No.: WO02/00900

PCT Pub. Date: Jan. 3, 2002

(65) Prior Publication Data

US 2003/0188345 A1    Oct. 2, 2003

(30) Foreign Application Priority Data

Jun. 28, 2000   (EP) .................................. 00113631

(51) Int. Cl.
*C12N 15/82* (2006.01)
*C12N 15/84* (2006.01)
(52) U.S. Cl. .................... 435/320.1; 435/469; 800/294
(58) Field of Classification Search ..................... None
See application file for complete search history.

(56) References Cited

U.S. PATENT DOCUMENTS

| 4,940,838 A | 7/1990 | Schilperoort et al. |
| 6,281,009 B1 * | 8/2001 | Boyce ..................... 435/320.1 |

FOREIGN PATENT DOCUMENTS

| EP | 0 120 516 | | 10/1984 |
| EP | 0 265 556 | | 5/1988 |
| EP | 1 136 560 | | 9/2001 |
| WO | WO99 01563 | * | 1/1999 |
| WO | WO99/01563 | | 1/1999 |
| WO | WO 01/44482 | | 6/2001 |

OTHER PUBLICATIONS

Xiang C. et al. A mini binary vector series for plant transformation. Plant Molecular Biology, vol. 40, No. 4, pp. 711-717, Jul. 1999.*
Hajdukiewicz et al. (1994, Plant Molecular Biology 25:989-994.*
Zambryski et al. (1982, Journal of Molecular and Applied Genetics, 1:361-370.*
Kononov et al. (1997, The Plant Journal 11:945-957.*
Gleave et al. (1999, Plant Molecular Biology 40:223-235.*
Xiang et al, "A mini binary vector series for plant transformation", Plant Molecular Biology, vol. 40, No. 4, Jul. 1999, pp. 711-717.

Jeong et al, "Construction of Small Binary Vectors for *Argobacterium*-Mediated Transformation of Plants", Journal of Plant Biology, vol. 42, No. 4, Dec. 1999, pp. 317-320.
Zambryski et al, "Tumor Induction by *Agrobacterium tumefaciens*: Analysis of the Boundaries of T-DNA", Journal of Molecular and Applied Genetics, vol. 1, No. 4, 1982, pp. 361-370.
Zupan et al, "Transfer of T-DNA from *Agrobacterium* to the Plant Cell", Plant Physiology, vol. 107, No. 4, Apr. 1, 1995, pp. 1041-1047.
Twigg et al., Trans-complementable copy-number mutants of plasmid ColE1, Nature, vol. 282, (1980).
Toro et al., Role of the overdrive sequence in T-DNA border cleavage in *Agrobacterium*, Proc. Natl. Acad. Sci., vol. 85, pp. 8558-8562, (1988).
Wang et al., Right 25 bp Terminus Sequence of the Nopaline T-DNA is Essential for and Determines Direction of DNA Transfer from *Agrobacterium* to the Plant Genome, Cell, vol. 38, 455-462, (1984).
Sauer, Site-specific recombination: developments and applications, Current Opinion in Biotechnology, 5:521-527 (1994).
Hajdukiewicz et al., The small, versatile pPZP family of *Agrobacterium* binary vectors for plant transformation, Plant Molecular Biology 25: 989-994, (1994).
Senecoff et al., Directionality in FLP Protein-promoted Site-specific Recombination Is Mediated by DNA-DNA Pairing, The Journal of Biological Chemistry, vol. 261, No. 16, Issue of Jun. 5, pp. 7380-7386, (1986).
Ramanathan et al., Transfer of non-T-DNA portions of the *Agrobacterium tumefaciens* Ti plasmid pTiA6 from the left terminus of $T_L$-DNA, Plant Molecular Biology 28: 1149-1154, (1995).
An et al., New cloning vehicles for transformation of higher plants, The EMBO Journal, vol. 4, No. 2, pp. 227-284, (1985).
Itoh et al., Genetic and Molecular Characterization of the Pseudomonas Plasmid pVS1, Plasmid 11, 206-220, (1984).
Peralta et al., Overdrive, a T-DNA transmission enhancer on the *A. tumefaciens* tumour-inducing plasmid, The EMBO Journal, vol. 5, No. 6, pp. 1137-1142, (1986)
Watson et al., Relationships of the Col Plasmids E2, E3, E4, E5, E6, and E7: Restriction Mapping and Colicin Gene Fusions, Plasmid 13, 205-210 (1985).
Gallego et al., Positive-negative selection and T-DNA stability in *Arabidopsis* transformation, Plant Molecular Biology 39: 83-93, (1999).

(Continued)

*Primary Examiner*—Ashwin Mehta
*Assistant Examiner*—Li Zheng
(74) *Attorney, Agent, or Firm*—Connolly Bove Lodge & Hutz LLP

(57) ABSTRACT

The present invention relates to a binary vector which is distinguished by the combination of a variety of elements, demonstrates particularly high compatibility from the cloning aspect and which, besides the T-DNA flanked by the right and left border, contains an additional sequence which makes possible highly efficient and correct transfer of the T-DNA.

6 Claims, 8 Drawing Sheets

OTHER PUBLICATIONS

Maas et al., The combination of a novel stimulatory element in the first exon of the maize Shrunken-1 gene with the following intron 1 enhances reporter gene expression up to 1000-fold, Plant Molecular Biology 16: 199-207, (1991).

Kononov et al., Integration of T-DNA binary vector 'backbone' sequences into the tobacco genome: evidence for multiple complex patterns of integration, The Plant Journal 11(5), 945-957 (1997).

Zupan et al., The transfer of DNA from *Agrobacterium tumefaciens* into plants: a feast of fundamental insights, The Plant Journal, 23(1), 11-28, (2000).

Tinland, The integration of T-DNA into plant genomes, Elsevier Science Ltd., vol. 1, No. 6, 178-184, (1996).

Hanson et al., A simple method to enrich an *Agrobacterium*-transformed population for plants containing only T-DNA sequences, The Plant Journal, 19(6), 727-734, (1999).

Martineau et al., On Defining T-DNA, The Plant Cell, (Letter to the Editor), pp. 1032-1033, (1994).

Sugita et al., A transformation vector for the production of marker-free transgenic plants containing a single copy transgene at high frequency, The Plant Journal, 22(5), 461-469, (2000).

Kononov et al., Integration of T-DNA binary vector 'backbone' sequences into the tobacco genome: evidence for multiple complex patterns of integration, The Plant Journal, 11(5), 945-957 (1997).

Bevan, Binary *Agrobacterium* vectors for plant transformation, Nucleic Acids Research, vol. 12, No. 22, (1984).

Becker et al., New plant binary vectors with selectable markers located proximal to the left T-DNA border, Plant Molecular Biology, 20: 1195-1197, (1992).

Höfgen et al., Storage of competent cells for *Agrobacterium* transformation, Nucleic Acids Research, vol. 16, No. 20, (1988).

Ke et al., High-efficiency gene transfer to recalcitrant plants by *Agrobacterium tumefaciens*, Plant Cell Reports, 20: 150-156, (2001).

Moloney et al., High efficiency transformation of *Brassica napus* using *Agrobacterium* vectors, Plant Cell Reports, 8: 238-242, (1989).

Hellens et al., pGreen: a versatile and flexible binary Ti vector for *Agrobacterium*-mediated plant transformation, Plant Molecular Biology 42: 819-832, (2000).

* cited by examiner

SEQUENCE LISTING

```
<160> NUMBER OF SEQ ID NOS: 2
<210> SEQ ID NO 1
<211> LENGTH: 113
<212> TYPE: DNA
<213> ORGANISM: Artificial Sequence
<220> FEATURE:
```

-continued

```
<223> OTHER INFORMATION: Description of Artificial Sequence:additional
      Border Sequence aBS

<400> SEQUENCE: 1
cagctgcttg gtaataattg tcattagatt gtttttatgc atagatgcac tcgaaatcag        60
ccaattttag acaagtatca aacggatgtt aattcagtac attaaagacg tcc             113

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence:part of
      additional Border Sequence aBS

<400> SEQUENCE: 2
tgcatagatg cactcgaaat cagccaattt tag                                    33
```

BINARY VECTORS FOR THE IMPROVED TRANSFORMATION OF PLANTS SYSTEMS

RELATED APPLICATIONS

This application is the U.S. national phase of international application (under 35 U.S.C. 371)PCT/EP01/07359 filed 28 Jun. 2001 which designated the U.S. and which claims benefit of European application 00113631.6 filed Jun. 28, 2000.

The present invention relates to a system of novel binary vectors characterized in that, despite their extraordinarily small size, they comprise all of the elements required for the transfer into the agrobacteria and the plant.

The transformation of plants with the aid of the agrobacteria-mediated gene transfer is described in the literature. The vectors, which are based on the agrobacterial Ti plasmids, permit the transformation of a wide range of plant species by exploiting a natural bacterial system for introducing DNA into the nuclear genome of plants. As part of this highly-developed parasitic behavior, the *agrobacterium* transfers a defined part of its DNA, namely the T-DNA, which is demarcated by 25 bp repeats, also termed left and right border, into the chromosomal DNA of the plants (Zupan et al., The Plant Journal 23(1), 11-28, 2000). The combined action of what are known as vir genes, which are located on the original Ti plasmids, make possible this DNA transfer of the T-DNA. *Agrobakterium*-mediated gene transfer exploits the advantages of this natural plant transformation system. To this end, what are known as binary vectors, which permit a more or less efficient transfer of useful gene or gene constructs, were constructed. Earlier studies revealed no irregularity with regard to the site at which the foreign DNA is incorporated into the genome of the plant DNA. It was demonstrated that the T-DNA, which is demarcated by repeats (left and right border), of the binary vector is transferred relatively accurately (Tinland et al., Trends in Plant Science 1(6), 178-184, 1996). Essential functional parts of the binary vector are the T-DNA together with the border repeats, and the prokaryotic vector sequences with the replication origins (ori) for the replication and maintenance in the bacteria (*E. coli* and *agrobacterium*).

The binary vectors described to date are based on the broad-host-range plasmids such as pRK252 (Bevan et al., Nucl. Acid Res. 12, 8711-8720, 1984) and pTJS75 (Watson et al., The EMBO Journal 4, No. 2, 277-284, 1985), which have a broad host spectrum and are derived from the P-type plasmid RK2. However, their disadvantage is that they are unstable under nonselective conditions (Ditta et al., Plasmid 13, 149-153, 1985). A large group of the binary vectors used is derived from pBIN19 (Bevan et al., Nucl. Acid Res. 12, 8711-8720, 1984), which, in addition to the border of the Ti plasmid pTiT37, contains the replication origin RK2, which is active in agrobacteria, together with the relevant cis elements $ori_V$ and $ori_T$ and the ColE1 origin from pBR322. Hajdukiewicz et al. developed a novel binary vector (pPZP) which was smaller and more effective than those conventionally used (Hajdukiewicz et al., Plant Molecular Biology 25, 989-994, 1994). Instead of the replication origin RK2, the vector pPZP described therein has the replication origin of the Pseudomonas plasmid pVS1, which displays the typical organization for complete partition locus and thus factors for stable inheritance in the agrobacteria over generations (Itoh et al., Plasmid 11, 206-220, 1984). Owing to its complete partition system, the pVS1 segment confers the genetic stability over generations without selection pressure. This characteristic, which RK2-based binary vectors lack, appears to be essential for a higher transformation rate in oilseed rape.

Earlier analyses of the sequences required for the transfer confirmed that only two cis-acting elements are essential. These two 25 bp direct, not quite identical repeats (also known as borders) flank the T-DNA. Any DNA located between those borders is transferred in a directed fashion (Wang et al., Cell 38, 455-462, 1984). While the right border is always necessary and is cleaved very exactly, modifications on the left border do not necessarily prevent DNA transfer. The left end of the transferred DNA is more variable. This is why undesired vector sequences, for example bacterial resistance genes, are also transferred into the genome of the plants in addition to the T-DNA with the desired transgenic nucleotide sequences (Hanson et al., The Plant Journal 19(6), 727-734, 1999, Kononov et al., The Plant Journal 11, 945-957, 1997, Martineau et al., The Plant Cell 6, 1032-1033, 1994, Ramanathan et al., Plant Mol. Biol. 28, 1149-1154, 1995). However, when using these plants in agriculture, this is undesired, in particular for safety reasons. The systems known to date therefore require complicated molecular analyses of the transformed plants which have been generated if the latter are to be released for use in agriculture.

A further disadvantage of existing binary vectors is their size, which is difficult to handle, and their low copy number, for example the 12 kb pBIN19 (Bevan et al., Nucl. Acid Res. 12, 8711-8720, 1984) or the 13 kb pGA482 (An et al., The EMBO Journal 4, No.2, 277-284, 1985). The low copy number leads to low DNA yields of the plasmids and makes the cloning procedures difficult. Unstable replication origins may lead to variable plasmid loss during replication. While the vector pgreen, which is 4.6 kb in size, is very small, it lacks the elements for stable multiplication in agrobacteria, so that it can only be used together with specific agrobacterial strains (Helles et al., Plant Molecular Biology 42, 819-832, 2000).

There is frequently also a lack of a sufficient number of restriction enzymes for cloning the desired expression cassettes, or the vectors only permit the use of few selection markers. Moreover, the existing binary vectors lack the possibility of removing selection markers from the transgenic lines at a later point in time. Simple sequence analyses with standard primers are not possible since the binary vectors do not contain recognition sites for commercially available sequence primers. Unique restriction cleavage sites which are present on the T-DNA or in the vector in addition to multiple cloning sites and which make possible modular handling are absent, as are restriction cleavage sites which permit what is known as gene stacking.

It is thus an object of the present invention to provide a system which no longer has the abovementioned disadvantages.

We have found that this object is achieved in accordance with the invention by a novel system of binary vectors which are distinguished by their complexity and modularity and, inter alia, by an additional border sequence. The presence of certain unique restriction cleavage sites which are independent of the multiple cloning site, in the T-DNA, but also in the vector, flanking the T-DNA, opens up the possibility of inserting any desired modules. The combination of individual elements is novel.

A binary vector is understood as meaning in accordance with the invention a vector which is capable of replicating both in *E.coli* and in agrobacteria and which contains the elements required for the transfer into a plant system.

The invention also relates to a method for generating binary vectors which meet the above-described objective. Preferably, a binary vector according to the invention is generated in 3 steps:

In the first step, the T-DNA and adjacent segments of a vector from the pPZP family (Hajdukiewicz et al., Plant Molecular Biology 25, 989-994, 1994) are first deleted and other border-containing PCR fragments, a multiple cloning site and a unique site for cloning the selection markers are incorporated adjacent to the left border in such a way that the bacterial resistance marker of the vector is adjacent to the right border. In this context, the vector pSUN1 according to the invention is reduced in size in comparison with, for example, pPZP200, by 0.7 kb.

In the second step, all of the NotI sites and further regions of the vector, some of which are not functional, are removed by means of two different deletions (pSUN10). They also include the nic recognition site, the transfer origin for the conjugal plasmid transfer without which transfer to other bacteria by natural conjugation is no longer possible. This is a big advantage from the safety point of view in comparison with other binary plasmids, of which only the plasmid pGreen, being a pUC-derived vector lacking an nic recognition site, is no longer capable of conjugation (Hellens et al., Plant Molecular Biology 42, 819-832, 2000). In *E.coli*, the removal of this plasmid segment resulted in an increase in copy number from 1.5-3 fold in the plasmid pAT153 in comparison with the plasmid pBR322 (Twigg et al., Nature 283, 216-218, 1980).

The overdrive sequence of the Ti plasmid pTiA6 was inserted into this vector, known as a second-generation vector, when the NcoI site was removed. In cis, this sequence has a positive effect on the elimination of the T-DNA and thus on the transfer of the T-DNA (Toro et al., Natl. Acad. Sci. USA 85,8558-8562, 1985). The manipulations in this second step lead to a further reduction in size of the vector pSUN10 according to the invention.

In the third step, the recognition sites for recombinases such as, for example, the FRT recognition sites for FLP recombinase (Senecoff et al., The Journal of Biological Chemistry 261(16), 7380-7386, 1986) are introduced in order to make possible an elimination of the selection markers used (vector pSUN20 according to the invention).

The present invention thus relates to small vectors, preferably in sizes of from 2 to 12, especially preferably 3-9, very especially preferably 4-6 kb, for the efficient transformation of plant systems, comprising a T-DNA into which, if appropriate, a heterologous nucleotide sequence is inserted into an extensive polylinker surrounded by conventional sequence primers, and which T-DNA is flanked by a right and a left border.

The vectors according to the invention are furthermore distinguished by the fact that they may contain, in the T-DNA, expression cassettes for overexpressing and/or repressing foreign genes.

The binary vectors according to the invention are distinguished by an additional sequence (aBS, additional Border Sequence) as shown in SEQ ID No. 1, homologues, functional equivalents and/or modifications thereof. This aBS sequence is adjacent to. the left border in the T-DNA and makes possible precise integration of the T-DNA into the plant genome. For clarification purposes, a portion of approximately 520 nucleotides of the vector according to the invention is shown in FIG. 1. According to the invention, the additional sequence aBS encompasses a region of approx. 60 to 240 nucleotides, preferably 90 to 120 nucleotides and especially preferably approx. 120 nucleotides. A particular embodiment of this additional border sequence according to the invention is shown as SEQ ID No. 1. Furthermore, the additional border sequence according to the invention comprises a functional sequence motif which is indicated in FIG. 1 by a frame. An increased number of recombination events take place, within this sequence motif, between the T-DNA and the plant genome. This sequence motif according to the invention can vary within a region of between 15 to 50 nucleotides, preferably between 16 to [sic] 44 nucleotides, with at least 80%, preferably 90%, very especially preferably 95% and most particularly preferably 98% homology existing. In an especially preferred embodiment of the present invention, this sequence motif encompasses a region of 33 nucleotides, which is shown as SEQ ID No. 2. In the remaining regions, the additional nucleotide sequence according to the invention (aBS) can vary increasingly, an increased AT content having advantageous effects. The specific sequence information is only for illustration purposes, but has no limiting effect on the present invention. The present invention thus also relates to homologues, functional equivalents and/or modifications of the additional sequence according to the invention. Functional equivalents are understood as meaning, in accordance with the invention, nucleotide sequences which have essentially the same effect. Functionally equivalent sequences are the sequences which retain the desired functions despite deviating nucleotide sequences. Functional equivalents thus encompass naturally occurring variants of the sequences described herein, and also artificial nucleotide sequences, for example those obtained by chemical synthesis. A functional equivalent is also understood as meaning, in particular, natural or artificial mutations of an originally -isolated sequence which continue to exert the desired function. Mutations encompass substitutions, additions, deletions, exchanges or insertions of one or more nucleotide residues.

Other nucleotide sequences which are also encompassed by the present invention are, for example, those which are obtained by modifying the nucleotide sequence, resulting in corresponding derivatives. The purpose of such a modification may be, for example, the further demarcation of the sequence, or else, for example, the insertion of further cleavage sites for restriction enzymes.

The invention therefore furthermore relates to a binary vector characterized by polylinkers with more than 6, preferably 15-20, especially preferably 16-25, unique restriction cleavage sites.

Homologous sequences are understood as meaning, in accordance with the invention, those which are complementary to the nucleotide sequences according to the invention and/or hybridize therewith. In accordance with the invention, the term "hybridizing sequences" includes substantially similar nucleotide sequences from the group DNA or RNA, which undergo specific interaction (binding) with the above-mentioned nucleotide sequences under stringent conditions known per se. These also include short nucleotide sequences with a length of, for example, 10 to 30, preferably 12 to 15, nucleotides. In accordance with the invention, what are known as primers or probes are also included, inter alia.

Furthermore, the binary vector according to the invention comprises a T-DNA demarcated by the right and left border, where the additional sequence according to the invention may be adjacent to, for example, the left border. The right border may furthermore comprise what is known as a enhancing segment or "overdrive sequence" (Peralta et al., The EMBO Journal 5, 1137-1142, 1986), which has a beneficial effect on the efficacy of the T-DNA transfer and thus of the desired heterologous DNA which is present therein. In the exemplary embodiment of the T-DNA shown in FIG. 1, two singular recognition sites for restriction enzymes are additionally also found on both sides next to an extensive polylinker flanked by the uni and the reverse primers. These recognition sites can be used for example for integrating heterologous nucleotide sequences, selection markers and further modules such as, for example, elements for recombination, alternative selection systems (GST-MAT system, (Sugita et al., The Plant Journal 22(5), 461-469, 2000) or a second selection marker, between the polylinker and the border. Two other singular restriction cleavage sites are positioned, in the vectors according to the invention and their derivatives, adjacent to the T-DNA and permit the insertion of markers or suicide genes, which permit the integration into the plant DNA to be verified. These sites can also be utilized for integrating a further T-DNA and thus permit the independent integration of, for example, selection markers and transgenes. Another possibility is the integration of vir genes, which are supposed to make possible an improved transformation efficiency (Ke et al., Plant Cell Reports 20, 150-156, 2001). The vector according to the invention is furthermore distinguished by the fact that it may comprise, in the T-DNA, expression cassettes for overexpressing and/or repressing foreign genes. A further advantage of these vectors is the fact that the bacterial resistance gene is adjacent to the right border and thus, according to the mechanistic interpretations of the T-DNA transfer, far removed from the T-DNA which is being transferred. The vectors pSUN10 and pSUN20 according to the invention and their derivatives are distinguished firstly by the fact that, owing to deletions of unnecessary sequence segments in the vector moiety without the T-DNA, they are only 4.6 kb in size. They have all of the elements required for replication in E.coli (ColE1 origin) and in the agrobacteria (pVS1 origin) and for the transformation (modified left and right border) into the plant. The small size of the vectors according to the invention, the absence of frequently used restriction cleavage sites outside the T-DNA, the comfortable polylinker, the ColE1 origin and the high copy number of the plasmids which it entails allow other sequence segments to be cloned very readily into the vectors. The two further unique restriction cleavage sites PvuII and BglII in the T-DNA, which flank the multiple cloning site, and the two restriction cleavage sites MluI and NcoI (in pSUN10 SspI) which flank the T-DNA increase the modularity of the vectors. Features which are typical for the binary vectors according to the invention are the combination of small vector size, the presence of all elements which are necessary for its function, the absence of recognition sites for conventionally used restriction enzymes such as, for example, NotI outside the T-DNA, ease of handling owing to the high copy number in E.coli and the stability in agrobacteria, the very extensive polylinker, which has 18 unique restriction cleavage sites, the presence of recognition sites for commercially available sequencing primers flanking the polylinker, the polylinker-independent cloning of the selection marker next to the left border, and the position of the bacterial selection marker adjacent to the right border. The absence of the NotI sites in the vector opens up the possibility of establishing, in the T-DNA, a specific cassette which makes possible the cloning of cDNA and genomic libraries via the frequently used EcoRI/NotI adapters. The combination, according to the invention, of the sequence segments and the high modularity which this entails are novel.

The binary vectors according to the invention are furthermore distinguished by the fact that the vector pSUN20 and its derivatives has [sic] the recognition motifs for the recombination FRT of the FLP recombinase of the 2µ plasmid from the yeast Saccharomyces cerevisiae (Senecoff et al., The Journal of Biological Chemistry 261(16), 7380-7386), 1986) flanking the insertion site for the selection markers, and thus the possibility of removing the selection markers from the transgenic lines by recombination. Moreover, they have a unique restriction cleavage site such as, for example, ScaI between the polylinker and the left border for the insertion of selection markers which are subsequently transferred into the plant, behind the target gene, and thus permit the selection of transgenic plants which also comprise the target gene. Owing to their small size, the binary vectors according to the invention can also be employed efficiently for direct gene transfer. Suitable methods for doing so are known to the skilled worker, such as, for example, microinjection, electroporation, the fusion of protoplasts with liposomes, treatment of protoplasts with calcium phosphate, polyethylene glycol or other substances, and methods which promote introduction of the binary vectors into plant cells. Such methods are described, for example, in Rompp: Biotechnologie und Gentechnik [Biotechnology and recombinant techniques] Thieme Verlag Stuttgart, 2nd Ed., 1999, on pages 324-330. In a preferred variant, for example, the biolistic method is employed, for example for verifying promoter/reporter gene fusions by means of transient expression following the bombardment with DNA-loaded gold particles.

Owing to its modular construction, the vector according to the invention furthermore offers a large number of possibilities for integrating a variety of elements, such as, for example, the codA gene from E.coli, which encodes a cytosine deaminase and makes possible a combined positive/negative selection (Gallego et al., Plant Molecular Biology 39, 83-93, 1999), sequences which promote homologous recombination, for example the cre/lox system (Sauer et al., Current Opinion in Biotechnology 5, 521-527, 1994) or the FLP recombinase system (Maniatis, T., Fritsch, E. F. & Sambrook, J. *Molecular cloning—A laboratory manual* (Cold Springer Harbor Lab., Cold Springer Harbor, N.Y.), 1982). The singular restriction cleavage sites outside the T-DNA of the vector permit the integration of, for example, an RNAse gene which acts as a suicide gene (Barnase gene; (Hanson et al., The Plant Journal 19(6), 727-734, 1999), in order to suppress the transfer of vector sequences. Moreover, they offer the possibility of integrating vir genes, which should make possible an increased transformation efficiency in monocotyledonous plants (Ke et al., Plant Cell Reports 20, 150-156, 2001). Moreover, they also offer for example the possibility of integrating a second T-DNA in order to generate marker-free plants following cotransformation. The present invention thus also relates to a method for the effective transformation of monocotyledonous and dicotyledonous plant systems, where particularly small vectors, comprising a T-DNa with a polylinker with a great number of, for example more than 6, preferably 15-20, especially preferably 16-25, unique [sic] unique restriction cleavage sites into which, if appropriate, a heterologous nucleotide sequence (desired insertion) is inserted and which is flanked by a right border and a modified left border corresponding to pSUN1, as shown in SEQ ID No. 1, homologues, functional equivalents and/or modifications thereof, is [sic] transferred into a plant system and this vector [sic] mediates highly efficiently a transfer of the T-DNA which is flanked by the right and the left border and into which, if appropriate, the desired heterologous nucleotide sequence is inserted, into the genome of a plant system. The transformation of plants is a routine procedure for an ever increasing number of plant species, both monocotyledonous and dicotyledonous species. This invention also relates to those plant species which are as yet not accessible to genetic transformations. In principle, the present invention can be applied to any transformation method, whether the gene transfer is direct or indirect, into suitable plant cells. A method which is preferred in accordance with the invention is the *agrobacterium*-mediated gene transfer. The use of what is known as the binary vector technique, which is protected by patents EP A120516 and U.S. Pat. No. 4,940,838, is especially preferred.

The vectors according to the invention which are used in this method comprise, as further valuable elements in the T-DNA, recognition sites for customary sequence primers (pUC18 uni and reverse primers) and a further unique site, for example an ScaI site, for the integration of the selection markers adjacent to the left border, which site is flanked, for example, by the FRT recognition sites of the FLP recombinase of the 2μ plasmid from the yeast *Saccharomyces cerevisiae* and makes possible the removal of the selection markers at a later point in time by means of recombination. The vector pSUN20 which is used in this method and its derivatives likewise have the advantage of no customary restriction cleavage sites such as, for example, NotI, being present in the vector sequences outside the T-DNA. Thus, cassettes which permit the cloning of NotI/EcoRI-flanked cDNA and of genomic libraries might be established in the T-DNA. They are referred to hereinbelow as gene libraries.

Immediately on the vector side of the left border, there is an MluI site for the integration of negative markers, such as the coda gene from *E.coli*, which encodes a cytosine deaminase and permits a combined positive/negative selection (Gallego et al., Plant Molecular Biology 39, 83-93, 1999).

The present invention furthermore relates to a transformed plant system, to regenerated cells or a regenerated plant therefrom, to their progeny or seeds therefrom generated in accordance with a method according to the invention described hereinabove. In a particular embodiment of the present invention, this transformed plant system is characterized in that it should not comprise sequence segments of the abovementioned vector outside the right and/or left border.

The present invention furthermore relates to the use of the binary vector according to the invention for establishing gene libraries and their transformation of plants, preferably mediated by agrobacteria.

The present invention also relates to a variant of the binary vector in which the polylinker is replaced by a sequence of rare restriction cleavage sites and is thus particularly suitable for cloning several expression cassettes (gene stacking).

The present invention is characterized in greater detail by the examples which follow, but which are not limiting for the invention:

General methods:
 1. Cloning methods
 Recombinant DNA techniques and sequence analyses are carried out as described by Maniatis et al. (Maniatis, T., Fritsch, E. F. & Sambrook, J. *Molecular cloning—A laboratory manual* (Cold Springer Harbor Lab., Cold Springer Harbor, N.Y.) 1982) and the enzymes applied are used as per instructions. The basic vector used is the plasmid pPZP200 (Hajdukiewicz et al., Plant Molecular Biology 25, 989-994, 1994). The right and left borders were amplified from the plasmid pPZP200 or from the agrobacterial strain C58 (pTiC58) (DZMS 5172).

2. Bacterial strains
 The strain DH5α was used for the transformation into *E.coli*. For the transformation into agrobacteria by means of the freeze-fall-method, strains EHA101, EHA105, C58C1 [mp90] LBA4404 and GV3101 were used (Höfgen et al., Nucl. Acids Res. 16(20), 9877, 1988).

3. Plant transformation
 The agrobacteria-mediated gene transfer of *Nicotiana tabacum* was carried out by what is known as the leaf disk method and of *Brassica napus* by petiole transformation (Moloney et al., Plant Cell Reports 8, 238-242, 1989).

4. Analysis of the genomic DNA from transgenic plants
 The genomic DNA of the transgenic tobacco and oilseed rape plants was prepared as follows:
 Approx. 3-5 g of leaf material are reduced to a fine powder under liquid nitrogen, using a pestle and mortar. After the material has been transferred into a 50 ml centrifuge tube and 15 ml of extraction buffer (500 mM sodium chloride, 100 mM Tris-HCl pH 8.0; 50 mM EDTA, pH 8.0; 1 mM mercaptoethanol) has been added, the extract is mixed thoroughly. Then, 1 ml of 20% SDS solution is added, and the mixture is shaken and incubated for 10 minutes at 65° C. After addition of 5 ml of 5 M potassium acetate, the extract is mixed and placed on ice for 20 to 30 minutes. After centrifugation for 20 minutes at 12000 rpm, the supernatant is transferred through a Miracloth membrane into a fresh centrifuge glass. After addition of 10 ml isopropanol, the contents of the centrifuge glass are mixed and precipitated for 20 to 30 minutes at −20° C. The genomic DNA is removed by centrifugation for 20 minutes at 10000 rpm and the supernatant is discarded. The dried pellet is resuspended in 0.7 ml of 50×TE and transferred into a tube. Then, the RNA is removed after addition of 20 μl RNase (10 mg/ml), incubation for 30 minutes at 37° C., addition of 75 μl of 3 M sodium acetate, mixing and centrifugation for 15 minutes at 13000 rpm. The supernatant is transferred into a fresh tube and 500 μl of isopropanol are added. After precipitation for 5 minutes at room temperature, the genomic DNA is removed by centrifugation for 15 minutes at 10000 rpm and washed with 70% strength ethanol. The dried pellet is dissolved overnight in 200 μl of TE at 4° C., and the concentration and quality of the genomic DNA are determined.

As an alternative, genomic DNA was isolated using the DNeasy Plant Kit from Quiagen.

In a first step, the transgenic lines were identified by PCR, using gene-specific primers. The integration of the foreign DNA was studied by means of Southern blot analyses of 20 μg of DNA after suitable restriction cleavage had been carried out. Using the Universal Genome Walker Kit from Clontech, junctions between the T-DNA and plant DNA were isolated and subsequently sequenced.

5. β-Glucuronidase activity assay (GUS assay)
 The reporter gene β-glucuronidase is a bacterial enzyme which can be used in quantitative and in histochemical activity assays. Tissue samples were incubated overnight at 37° C. in 1 mM X-Gluc, 50 mM sodium phosphate (pH 7.0) and 0.1% Tween 20 and were then evaluated. Following extraction of the tissues, the glucuronidase activity in the transgenic lines was determined quantitatively as described (Jefferson et al., Plant Molec. Biol. Rep. 5, 387-405, 1987) on the basis of the conversion of 4-methylumbelliferyl-β-D-glucuronide.

6. Luciferase assay:
 The expression of the luciferase gene was analyzed using the Luciferase Assay System (E1500) from Promega, following the instructions.

Construction of the Binary Vector pSUN1 According to the Invention

Following linearization of the plasmid pPZP200 (Hajdukiewicz et al., Plant Molecular Biology 25, 989-994, 1994) using ScaI, the T-DNA and adjacent sequence segments were degraded using nuclease Bal31. After the product had been made blunt-ended using the DNA polymerase Klenow fragment, the plasmid which remained was recircularized using the linker 5'-ttccatggtcagatctagtactcagctgagacgtcttacgcgtt-3' (SEQ ID NO: 17) (step I). The recircularization gave the plasmid pUH41 (FIG. 2). Unique restriction cleavage sites into which the borders, the polylinker and selection markers are introduced at a later point in time are located on this linker.

The subsequent transformation of E.coli and selection on spectinomycin (100 mg/l) only gave rise to clones which contained the complete resistance gene aadA aminoglycoside-3"-adenyl transferase.

The analysis of these colonies revealed that clone pUH41 showed the most extensive deletion, demonstrated very good resistance and was readily transformed into the agrobacterial strain EHA105. The borders were introduced into this clone.

To this end, the right and left borders were amplified from plasmid pPZP200 (Hajdukiewicz et al., Plant Molecular Biology 25, 989-994, 1994) using Advantage Tth Polymerase (Clontech) and the primers RB5/RB3 and LB5/LB3, respectively. After the PCR fragments have been cloned into the vector pUC18, the sequences were verified. The primers employed for the amplification of the right and the left border are stated hereinbelow:

Primer RB5: 5'-gagcttagatctgattgtcgtttcccgccttc-3' (SEQ ID NO: 3);

Primer RB3: 5'-cctgtggttgccatggacatacaaatggacg-3' (SEQ ID NO: 4),

Annealing temperature (Ta)=56° C.

Primer LBS5:5'-ctgatgggctgcctgtaacgcgtggtgattttg-3';

Primer LB3: 5'-cattaaagacgtccgcaatgtgttattaagttg-3',

Annealing temperature Ta=50° C.

The right border was cloned into the polylinker of the vector pUH41 via NcoI/BglII (FIG. 2, step II). After cleaving the resulting plasmid pDE44RB with AatII/MluI, the left border was inserted into it (step III). The 35S promoter phosphinothricin acetyltransferase 35SpA cassette was incorporated into the PvuII site of the resulting plasmid pUH45 in order to verify the integration and regeneration in a subsequent tobacco transformation (pUH56, FIG. 2, step VI).

In order to be able to use a large number of unique restriction cleavage sites in the polylinker, the linker 5'-gtacctcggcccgggcgatatcggatccactagt-3' (SEQ ID NO: 18) was cloned into the XbaI- and Asp718-cut vector pUC19. The polylinker, which contains the sites EcoRI SacI KpnI XhoI SrfI SmaI EcoRV BamHI SpeI XbaI SalI HincII PstI SseI SphI HindIII, was amplified via the universal and reverse M13 primers and ligated into the ScaI site of pUH45 (step IV).

Owing to the two possible orientations of the polylinker, this gave rise to the piasmids pUH52 (FIG. 2) and pUH53 (not shown).

To isolate the additional sequence (additional left border sequence), a PCR amplification using the primers SLB5: 5'-gcggacgtctttaatgtactgaattaacatccg-3' (SEQ ID NO: 7)

SLB3: 5'-cacagctgcttggtaataattgtcattagattg-3' (SEQ ID NO: 8)

were carried out on the isolated plasmid DNA of the DZMZ—pTi plasmid of Agrobacterium tumefaciens strain C58 (DSM No.: 5172) at a Ta of 55° C. The PCR product was cloned into the plasmid pUC18SmaI. According to sequence analysis, clone pUH46 showed the correct sequence.

Following cleavage with PvuII/AatII, the PvuII/AatII fragment of plasmid UH46, and thus the additional border sequence according to the invention, was incorporated into the plasmids UH52 and UH53, resulting in the vectors pSUN1 (FIG. 2, step V) and pUH58 (not shown).

Transformation of the Plasmid pUH56 into Tobacco

To test whether the modification of the border has an effect on callus formation and regeneration, the plasmids pUH56 (FIG. 2), which has [sic] a 35S phosphinothricin acetyltransferase cassette in the plasmid UH45 (FIG. 2), and, as a control, pPZP200::35SPat (corresponds to vector pUH 39), were transformed into the agrobacterial strain EHA 105. Nicotiana tabacum was transformed using the leaf disk method. FIG. 3 shows the regenerating shoots 3 and 6 weeks post-transformation in comparison with the control (pUH39). Regeneration proceeded without discernible differences between the regenerates. Thus, the modification of the borders had no adverse effect on regeneration.

Verification of the Transformation Efficiency and the Correct Insertion of the T-DNA The expression of the reporter genes glucuronidase and luciferase was exploited to detect firstly the efficiency of the novel vectors in transferring a transgene (glucuronidase, GUS) and secondly by the incorporation on the vector side of the left border of the T-DNA (luciferase, Luc), to prove that no vector sequences have been transferred concomitantly. The cloning steps required for the incorporation of the cassettes 35S promoter/glucuronidase and 35S promoter/ luciferase are understood from FIG. 4. pUH52 and pSUN1 were linearized with MluI, made blunt-ended, dephosphorylated and ligated with the blunt-ended HindIII fragment from the vector pRT101Luc (Maas et al., Plant Mol. Biol. 16, 199-207, 1991) (step I). Then, the blunt-ended EcoRI/ HindIII fragment of the plasmid pGUSINT37 was cloned into the SrfI site of the resulting plasmid pUH62 and, correspondingly, pUH61, giving rise to the plasmids pUH64 and, correspondingly, pUH63 (step II). The nosP/Pat/nosT (HindIII, blunt-ended) and, respectively, the nosP/NPTII/ nosT (HindIII/BamHI, blunt-ended) cassettes were integrated into these constructs into the PvuII site to act as selection markers (step III). The resulting clones pUH68 and pUH67, or pUH76 and pUH77, respectively, were transformed into the agrobacterial strains EHA101 and GV3101, respectively, and then into tobacco, Arabidosis and Brassica napus, respectively.

The transformed plants were grown in the greenhouse, with 70-90% of the shoots forming roots. 80-100% of the selected plants were transgenic for the selection marker. The glucuronidase and luciferase activities were determined as above. 70-90% of the plants showed GUS activity, and genomic PCR demonstrated integration of the GUS gene in 90-100% of the analyzed plants. The correlation between the resistant plants and the glucuronidase-expressing plants is thus very high, which indicates that the transfer of the T-DNA was complete. This was achieved by cloning the selection markers adjacent to the left border. Since the transfer of the T-DNA starts at the right border, the reporter gene is transferred first, followed by the gene of the selection marker (Becker et al., Plant Mol. Biol. 20, 1195-1197, 1992). This is also confirmed by genomic PCR and Southern analyses.

Any luciferase activity in the transgenic plants means that at least this part of the vector is integrated into the genome. When the transgenic tobacco plants which had been transformed with the vectors pUH67 and pUH68 according to the invention were analyzed, no luciferase activities were detected. However, approximately 30% of the oilseed rape plants which were analyzed showed luciferase activity. Genomic analyses confirmed that 30-50% of the transgenic plants may also comprise vector sequences. This agrees with data from the literature (Martineau et al., The Plant Cell 6, 1032-1033, 1994, Ramanathan et al., Plant Mol. Biol. 28, 1149-1154, 1995, Kononov et al., The Plant Journal 11, 945-957, 1997).

Construction of the Binary Vector pSUN10 According to the Invention

A fragment of the pVS1 origin was amplified from the plasmid pSUN1 in cloning step I (FIG. 5) by PCR. The primers used, PVS5a 5'-cgagcgacgcgtctaaaaaggt-3' (SEQ ID NO: 9) and PVSBsp 5'-caggggccccttgccacgattcaccgggg-3' (SEQ ID NO: 10), correspond to positions 1093-1105 and 2390-2371 on the plasmid pSUN1. This MluI/BSP120I-cleaved PCR fragment was cloned instead of the deleted 1878 bp fragment into the piasmid pSUN1, which previously cleaved with MiuI and partially with NotI. This gave rise to the plasmid pSundel. The overdrive sequence of the octopine plasmid pTiA6 (Toro et al., Proc. Natl. Acad, Sci. USA 85, 8558-8562, 1985) was cloned, with the aid of the oligos ov_RB 5'-catgataagtcgcgctgtatgtgtttgtttgaatatt3' (SEQ ID NO: 13) and ov_Ssp 5'-catgaatattcaaacaaacacata-cagcgcgacttat-3' (SEQ ID NO: 14), into the NcoI site, which was removed in the process (step II). In the resulting plasmid pSUNdelov, the SspI site is available as new unique restriction cleavage site adjacent to the right border in order to insert further bacterial selection markers, T-DNAs or other modules at this position.

In cloning step III, a further 336 bp and the nic site, the origin for conjugations with other bacteria, was [sic] deleted by cleavage with NotI and partial cleavage with NdeI, making the product blunt-ended and recircularizing the plasmid. Thus, these vectors and their derivatives can no longer be spread via conjugation, and biosafety is increased substantially. This gave rise to the plasmid pSUN10, which differs from plasmid pSUNI by the deletion of two sequence segments including the nic site and the integrated overdrive of the Ti plasmid pTiA6. The T-DNA was not modified in the process.

Construction of the Binary Vector pSUN20 According to the Invention

The purpose of this cloning step was to have available the possibility of removing the selection marker from the transgenic lines at a later point in time. The yeast FLP/FRT recominase system was used here by way of example (Senecoff et al., The Journal of Biological Chemistry 261 (16), 7380-7386, 1986). To do so, the FRT recognition sites had to be synthesized with the aid of oligos and cloned. To do so, a recognition site was first generated with the aid of the oligos 5'-gaagttcctatactttcttgagaatag-gaacttcggaataggaacttcgtcgacgtac-3' (SEQ ID NO: 15), 5'-cagtcgacgaagttcctattccgaagt-tcctattctcaagaaagtataggaacttcgtac-3' (SEQ ID NO: 16) and cloned into the KpnI site of the plasmid pOCS1. Then, the second recognition site, which had also been generated from oligos, was cloned, via XhoI ends, into the SalI site flanking the first FRT recognition site. The oligos have the following sequences: FRTII-1 5'-tcgagtactgaagttcctatactttct-tgagaataggaacttcggaatag-3' (SEQ ID NO: 11) and FRTII-2 5'-tcgagtgaagttcctattccgaagttcctattctcaagaaagtataggaa-3' (SEQ ID NO: 12).

This gave rise to the plasmid PFRTII, whose sequence was verified. The fused recognition sites were then excised in the form of an SmaI/Ecll36II fragment and cloned into the PvuII site of pSUN10 (FIG. 6).

Thus, the resulting plasmid pSUN20 differs from pSUN10 only by the additional sequence of the FRT recognition sites of plasmid pSUN10. The ScaI site between the FRT recognition sites is used for cloning the selection marker.

Proof for stable replication in *Agrobakterium tumefaciens*

Since parts of the pVS1 sequence segment were deleted, the intention is to demonstrate that this has no effect on the replication and the stability of the binary plasmid according to the invention in the agrobacteria. The vector pSUN10 according to the invention was transformed into the agrobacterial strains strains [sic] EHA101, EHA105, C58C1 [mp90] LBA4404 and GV3101 by freezing/thawing. After approximately 2 days, the colonies had grown normally. Three colonies of EHA101/pSUN10 were selected, grown in 5 ml YEB medium supplemented with 50 mg/l kanamycin and 100 mg/l [lacuna], and the plasmid DNA was isolated. After cleavage and verification, 100 µl aliquots were removed from these cultures in order to inoculate 100 ml of YEB medium. For each sample, one flask was treated with kanamycin/spectinomycin and one flask with kanamycin. Only agrobacteria which contain the binary plasmid were capable of growing in the first flask, owing to the spectinomycin resistance while the second flask also permitted the growth of EHA101 cells which had lost the plasmid.

Following overnight culture, the agrobacteria were plated on Petri dishes containing YEB medium in accordance with their resistances and in a variety of dilutions. The Petri dishes with the dilutions $10^{-8}$ and $10^{-9}$ were evaluated. This procedure was repeated 5 more times, so that 6 generations were analyzed. Plasmid DNA whose quality and quantity is indistinguishable was isolated from all samples of the last generation. FIG. 8 compiles the data in a diagram. The height of the bars shows the colonies counted; no significant difference was found between the conditions which are under [sic] nonselective for the binary plasmid pSUN10 and under selective conditions.

Construction of the pSUN20OTest

A construct was generated as shown in FIG. 7 for testing the novel vector pSUN20 according to the invention.

The SpeI/AatII fragment of the plasmid UH77, which contains an intron-containing GUS gene under the control of the 35S promoter and the NPTII gene under the control of the NosP, was cloned into the SmaI site of the vector pSUN20 (step I). The selection marker phosphinothricin acetyltransferase under the control of nosP was cloned into the ScaI site of the resulting plasmid pSUN20GUS between the FLP recombinase recognition sites (step II).

The resultant plasmid was transformed into tobacco. The transformed plants were grown in the greenhouse, and the glucuronidase activity was determined as above. The correlation between the phosphinothricin- and NPTII-resistant and glucuronidase-expressing plants was very high, meaning that all of the T-DNA had been transferred. This is also confirmed by the genomic PCR and Southern analyses. The progeny was hybridized with recombinase-expressing plants, and GUS expression was analyzed in the plants which are no longer phosphinothricin-resistant. It was demonstrated that these plants contain the target gene and that the excision of the selection marker was successful.

The abbreviations used have the following meanings:
AadA: Spectinomycin/streptomycin resistance
RB: Right border.
aBS: Additional nucleotide sequence; additional border sequence
sta: Partitioning protein
rep: pVS1 replication protein
pVS1: Replication origin of plasmid pVS1 with a broad host spectrum
ori: Replication origin ColE1
Singular recognition sites for restriction enzymes are also shown.

Figure 1:
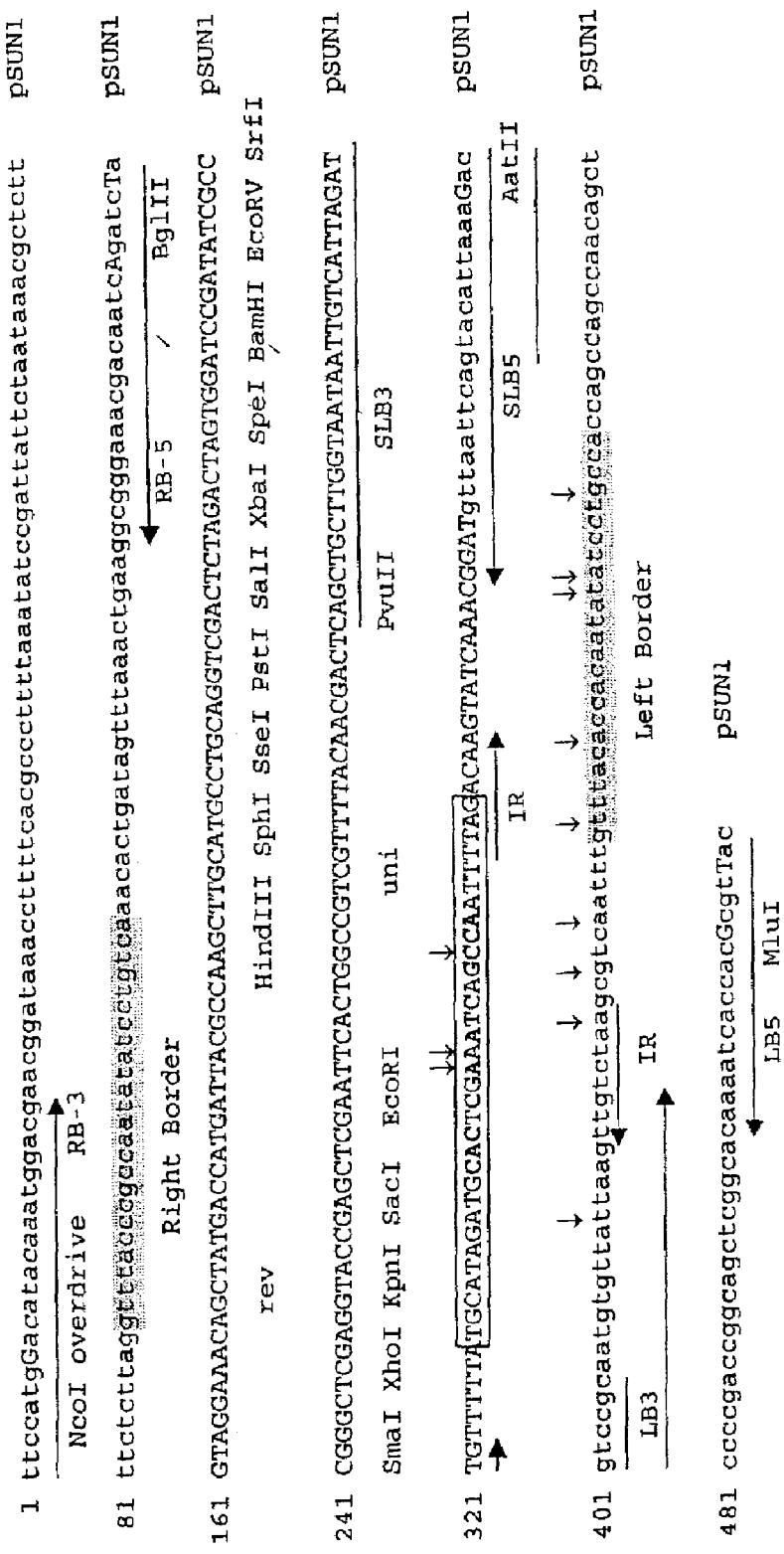
FIG. 1: Sequence segment from the vector pSUN1 (SEQ ID NO: 19) according to the invention containing the sequence aBS which is additional in accordance with the invention The abbreviations used have the following meanings:
RB-3; RB-5: Primers for the amplification of the right border
LB-3; LB-5: Primers for the amplification of the left border
SLB3:SLB5: Primers for the amplification of the sequence which is additional in accordance with the invention; additional Border Sequence (aBS)
Rev: Reverse sequence primer
Uni: Universal sequence primer
IR: Inverted repeat ↓: Junctions of T-DNA and the genome of transgenic plants
Figure 2:
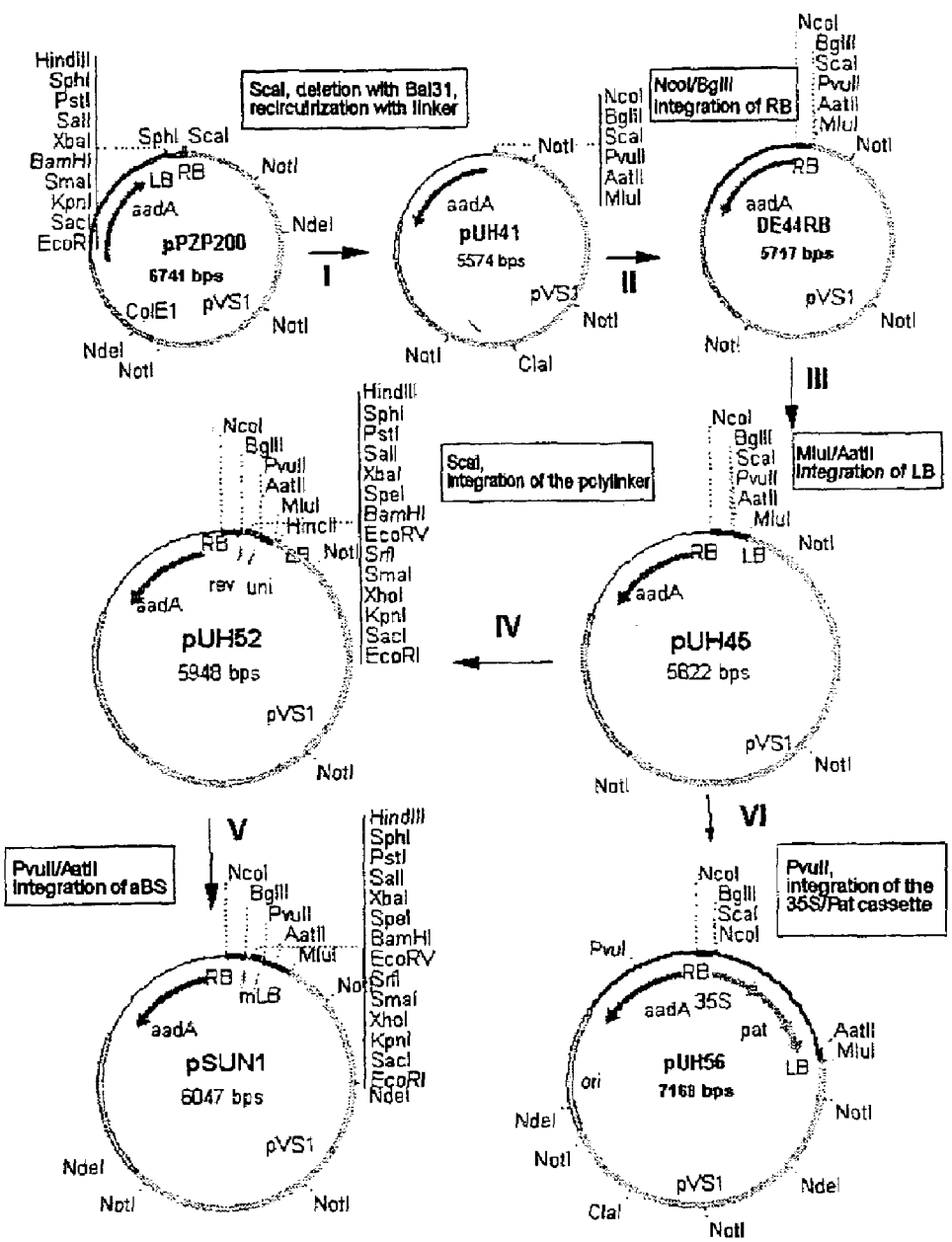
FIG. 2: Schematic representation of the construction of the binary vector pSUN1.
Figure 3:
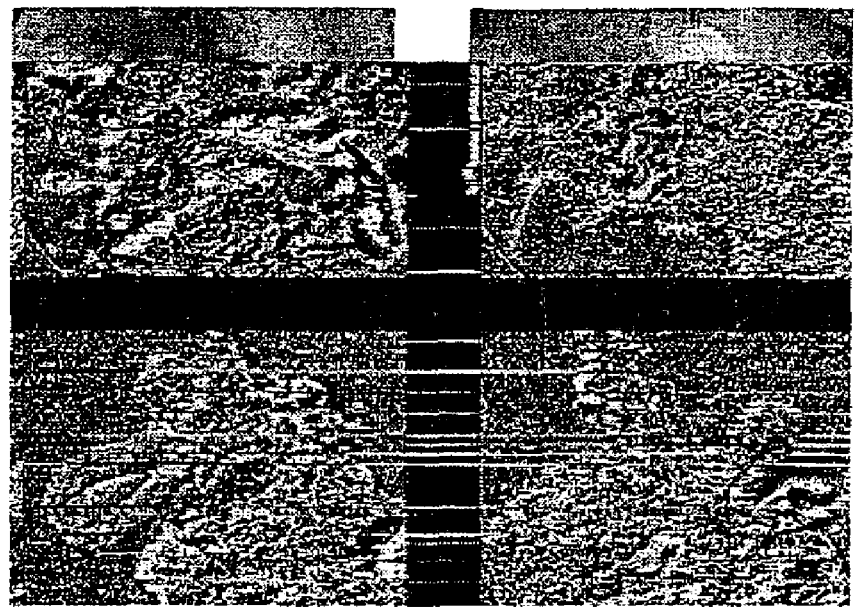

FIG. 3: Comparison of the regeneration of tobacco transformed with the vectors pUH56 and pUH39 (control) after 3 and 6 weeks.

Figure 4:
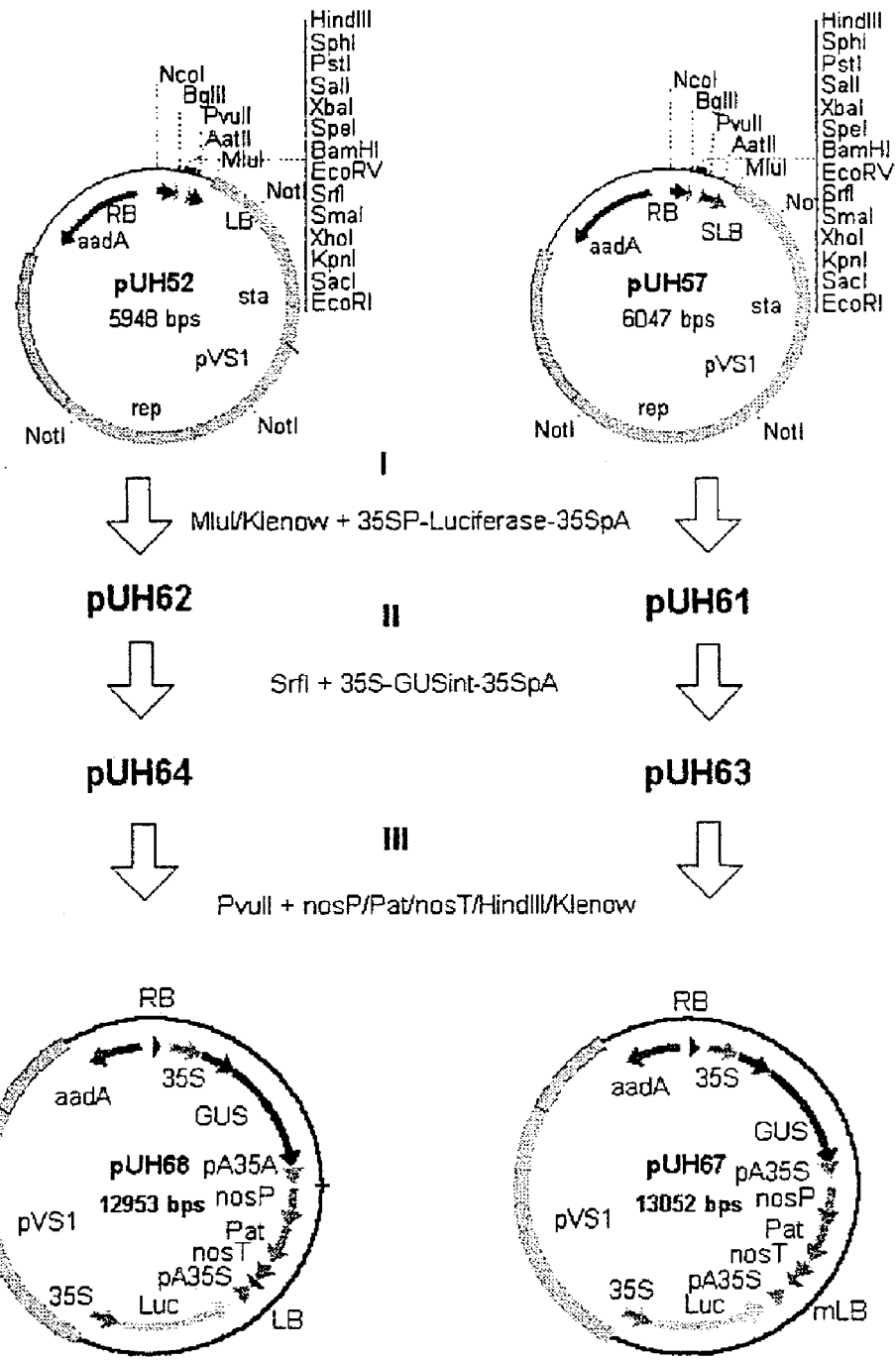

FIG. 4: Schematic representation of the construction of the binary vectors pUH68 and pUH67

The abbreviations used have the following meanings:
AadA: Spectinomycin/streptomycin resistance
RB: Right border
LB: Left border
aBS: Border sequence which is additional in accordance with the invention
35S: Cauliflower mosaic virus 35S RNA promoter
pA35S: Cauliflower mosaic virus 35S RNA terminator
nosP: Promoter of the *Agrobacterium tumefaciens* nopaline synthase gene
nosT: Transcription terminator of the *Agrobacterium tumefaciens* nopaline synthase gene
GUS: Reporter gene encoding the *E.coli* β-glucuronidase
Luc: Reporter gene encoding the firefly luciferase
Pat: Phosphinothricin acetyltransferase gene, synthetic
rep: pVS1 replication protein
pVS1: Replication origin of plasmid pVS1 with a broad host spectrum
ori: Replication origin ColE1
Singular recognition sites for restriction enzymes are also shown.

Figure 5:
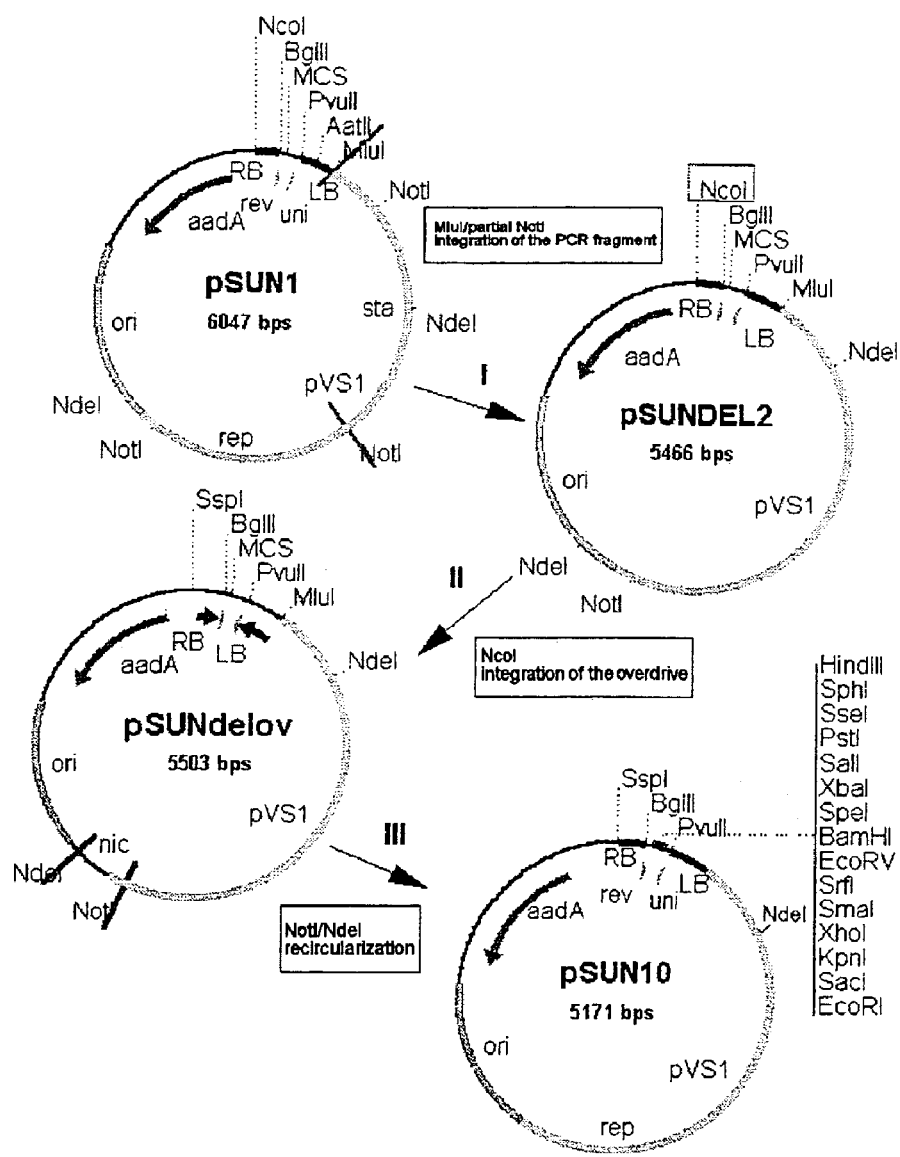

FIG. 5 Schematic representation of the construction of the binary vector pSUN10

The abbreviations used have the following meanings:
aadA: Spectinomycin/streptomycin resistance
RB: Right border
LB: Left border
MCS: Multiple cloning site
pVS1: Replication origin of plasmid pVS1 with a broad host spectrum
ori: Replication origin ColE1
Singular recognition sites for restriction enzymes are also shown.

Figure 6:
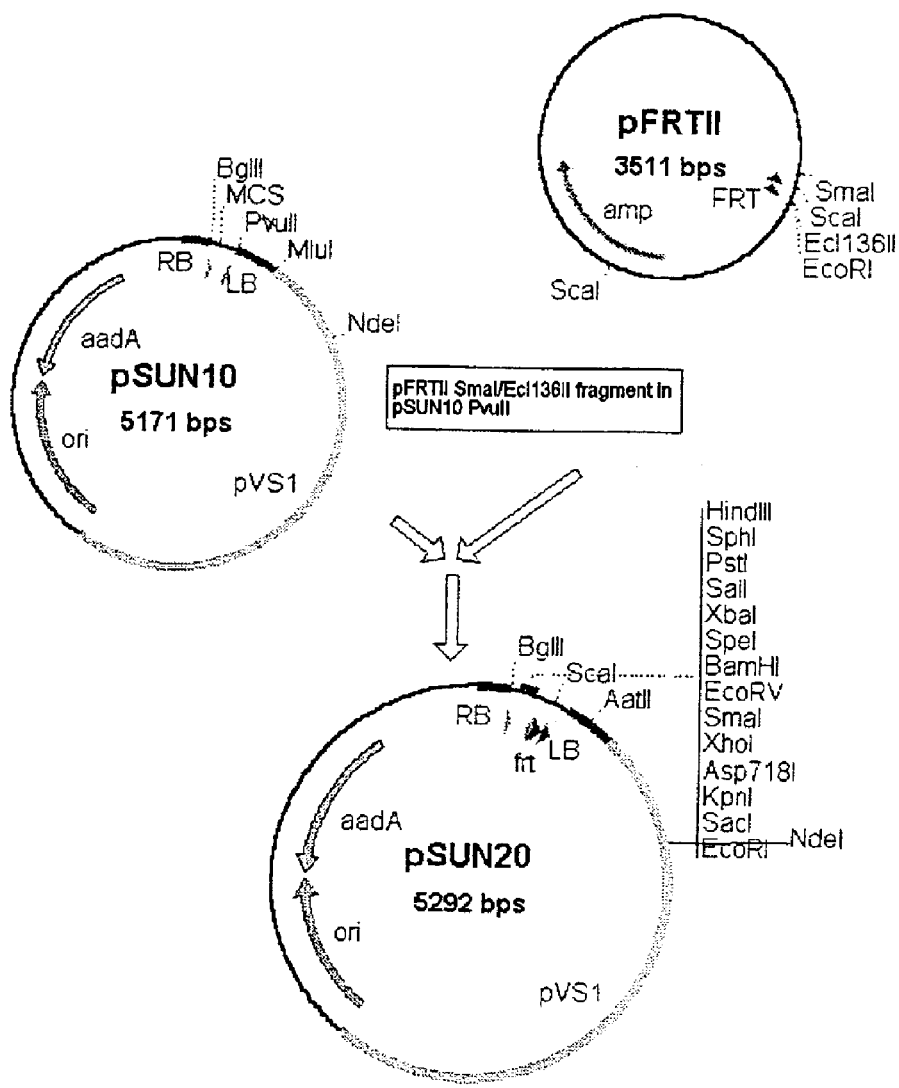

FIG. 6 Schematic representation of the construction of the binary vector pSUN20

The abbreviations used have the following meanings:
aadA: Spectinomycin/streptomycin resistance
RB: Right border
LB: Left border
MCS: Multiple cloning site
pVS1: Replication origin of plasmid pVS1 with a broad host spectrum
ori: Replication origin ColE1
frt: Recognition sites for the yeast FLP recombinase
Singular recognition sites for restriction enzymes are also shown.

Figure 7:
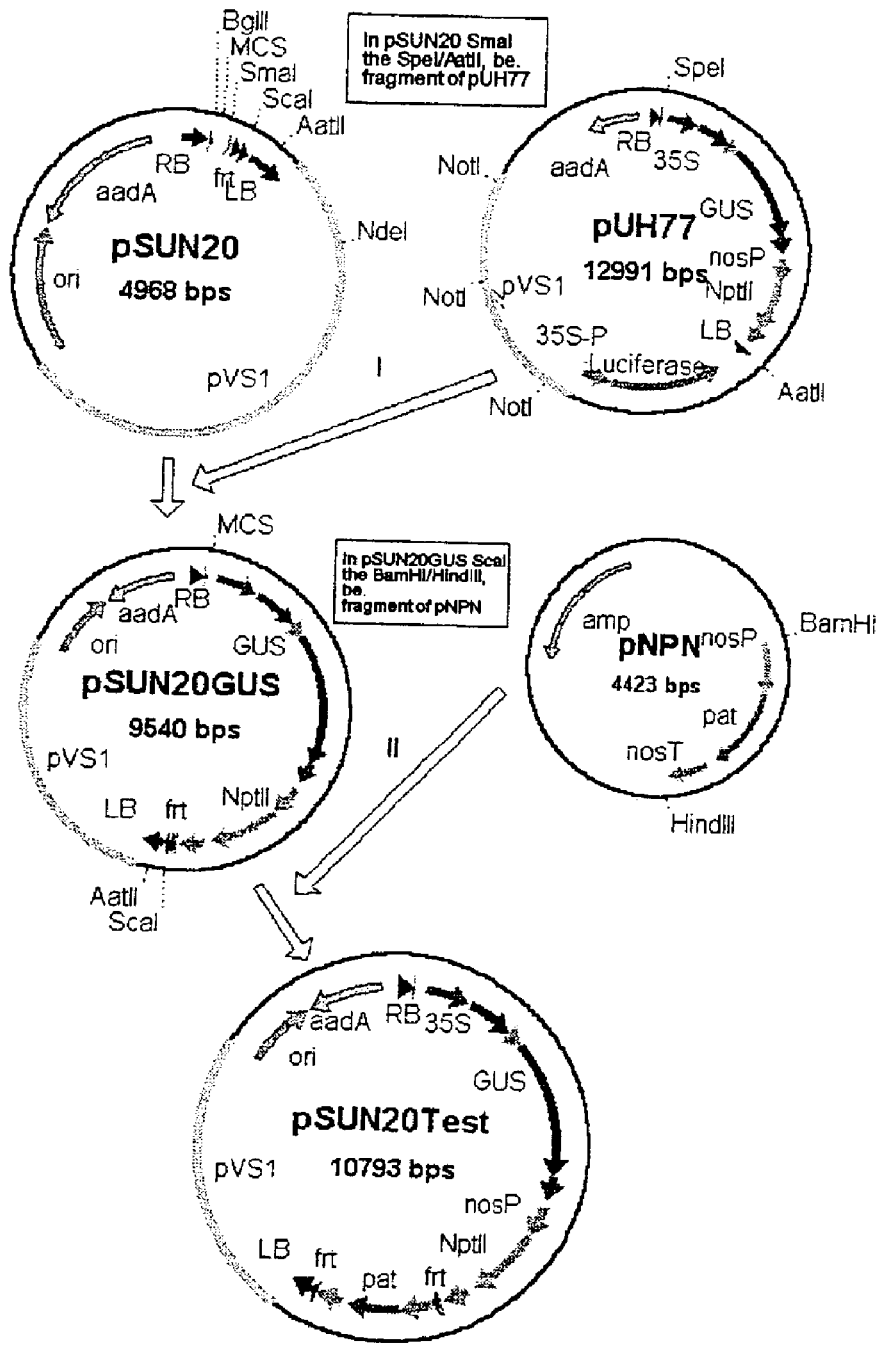

FIG. 7 Schematic representation of the construction of the binary vector pSUN20OTest AadA: Spectinomycin/streptomycin resistance
RB: Right border
LB: Left border
aBS: Border sequence which is additional in accordance with the invention
35S: Cauliflower mosaic virus 35S RNA promoter
pA35S: Cauliflower mosaic virus 35S RNA terminator
nosP: Promoter of the Agrobacterium tumefaciens nopaline synthase gene
nosT: Transcription terminator of the *Agrobacterium tumefaciens* nopaline synthase gene
GUS: Reporter gene encoding the *E.coli* β-glucuronidase
NptII Neomycin phosphotransferase gene
Pat: Phosphinothricin acetyltransferase gene, synthetic
rep: pVS1 replication protein
pVS1: Replication origin of plasmid pVS1 with a broad host spectrum
ori: Replication origin ColE1
frt: Recognition sites for the yeast FLP recombinase
Singular recognition sites for restriction enzymes are also shown.

Figure 8:
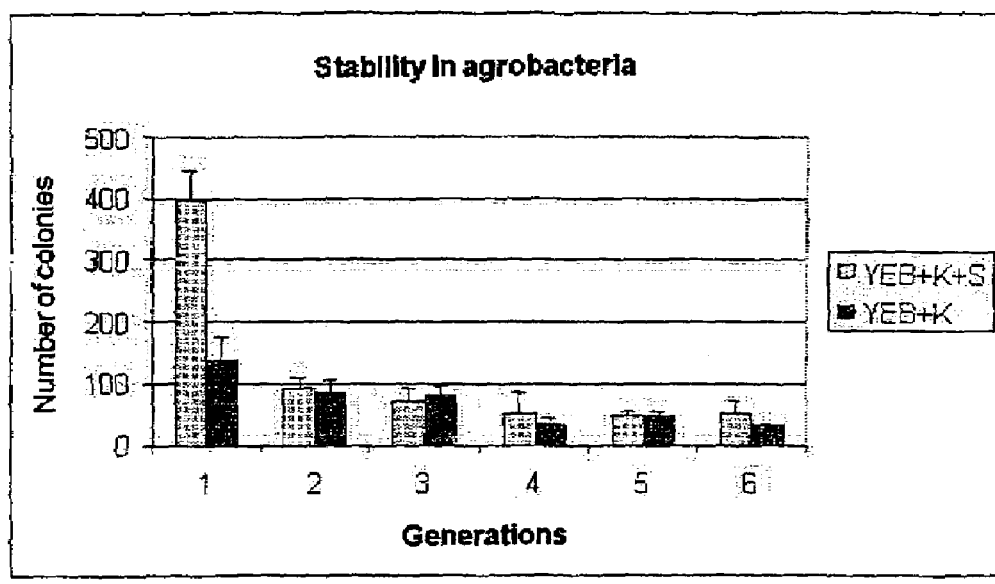

FIG. 8 Representation of the stability of the agrobacteria
YEB: Medium
K: Selected on kanamycin
K+S: selected on kanamycin and spectinomycin

We claim:

1. A binary vector for the transformation of plant systems, comprising a T-DNA into which a heterologous nucleotide sequence is inserted and which is flanked by a right and a left border, an additional sequence as shown in SEQ ID NO: 1 adjacent to the left border, and a polylinker with more than 6 unique restriction cleavage sites, wherein the additional sequence and the polylinker are between the right and the left border of the T-DNA.

2. The binary vector as claimed in claim 1, wherein the vector has a size of 2 to 12 kb.

3. The binary vector as claimed in claim 1, wherein the polylinker has more than 15 unique restriction cleavage sites.

4. A method for transforming plants or plant cells comprising transforming a plant or a plant cell with the binary vector as claimed in claim 1.

5. The method of claim 4, wherein the transformation is mediated via Agrobacteria.

6. A method for producing the vector of claim 1 comprising incorporating into a vector a T-DNA into which a heterologous nucleotide sequence is inserted and which is flanked by a right and a left border, an additional sequence as shown in SEQ ID NO: 1 adjacent to the left border, and a polylinker with more than 6 unique restriction cleavage sites, wherein the additional sequence and the polylinker are between the right and the left border of the T-DNA.

* * * * *